US00PP15293P2

(12) United States Plant Patent
Gibb

(10) Patent No.: US PP15,293 P2
(45) Date of Patent: Nov. 2, 2004

(54) ***GAILLARDIA* PLANT NAMED 'SUMMERS KISS'**

(50) Latin Name: *Gaillardia grandiflora*
Varietal Denomination: Summers Kiss

(76) Inventor: Katherine Gibb, 2035 Swimley Rd., Berryville, VA (US) 22611

( * ) Notice: Subject to any disclaimer, the term of this patent is extended or adjusted under 35 U.S.C. 154(b) by 0 days.

(21) Appl. No.: 10/405,118

(22) Filed: Mar. 31, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya

(57) ABSTRACT

A new cultivar of *Gaillardia* named 'Summers Kiss' that is distinguished by medium-green colored leaves, upright low-growing habit and large daisy-like flowers that are a melon color and that bloom in summer and fall. In combination these traits set 'Summers Kiss' apart from all other existing varieties of *Gaillardia* known to the inventor.

2 Drawing Sheets

Genus: *Gaillardia.*
Species: *grandiflora.*
Denomination: 'Summers Kiss'.

BACKGROUND OF THE INVENTION

The present invention relates to a new and distinct cultivar of blanket flower, an herbaceous perennial that is grown for use as an ornamental landscape and container plant. The new invention is known botanically as *Gaillardia grandiflora* and will be referred to hereinafter by the cultivar name 'Summers Kiss'. *Gaillardia* is in the family Compositae, under which the commonly referred to "flower" is actually the inflorescence, and made up of smaller ray flowers and disc florets. The ray florets are what look like "petals". For ease of clarification the common term "flower" is used herein to describe the inflorescence.

'Summers Kiss' is a chance seedling that was discovered by the inventor in 1997 in a cultivated area of Maryland. The inventor discovered the seedling in a large crop of seed grown *Gaillardia* 'Goblin' (not patented) that were on a propagation bench in the inventor's greenhouse. The female parent plant is presumed to be *Gaillardia* 'Goblin' and the male parent plant is presumed to be *Gaillardia* 'Goblin'. 'Summers Kiss' differs from the parent plants in flower color.

'Summers Kiss' exhibits a low-growing, upright habit and large daisy-like flowers that open pink-orange in color and age to melon. The flower color has been characterized, by some, to be peach, apricot and sunset. Blooming occurs from mid summer into fall. Cultural requirements include full sun to light shade, moderate water and well-draining soil. Hardiness is classified as USDA Zone 5.

The distinguishing characteristic of 'Summers Kiss' is the flower color. The closest comparison plant is the presumed sport parent *Gaillardia* 'Goblin'. 'Summers Kiss' is distinguishable from *Gaillardia* 'Goblin' by flower color. The petals of the flowers of *Gaillardia* 'Goblin' are red (close to Red Group 44A, The Royal Horticultural Colour Chart 2001 Edition) with yellow edges and tips. The petals of the flowers of 'Summers Kiss' are apricot colored (close to Orange Group 25D, The Royal Horticultural Colour Chart 2001 Edition). A second comparison cultivar of similar form and function to 'Summers Kiss' in *Gaillardia* 'Golden Goblin' whose flowers are pale lemon-yellow.

The first asexual reproduction of 'Summers Kiss' was carried out by the inventor in 1997 in a cultivated area of Maryland. The method used was softwood cuttings. Cuttings were placed in sandy soil, under light mist with bottom heat in the inventor's greenhouse. Since that time subsequent generations have been determined stable and true to type.

SUMMARY OF THE INVENTION

The following traits have been repeatedly observed and represent the distinguishing characteristics of the new *Gaillardia* cultivar. These traits in combination distinguish 'Summers Kiss' from all other existing varieties of *Gaillardia* known to the inventor. 'Summers Kiss' has not been tested under all possible conditions and phenotypic differences may be observed with variations in environmental, climatic, and cultural conditions, however, without any variance in genotype.

1. *Gaillardia* 'Summers Kiss' is an herbaceous perennial.
2. *Gaillardia* 'Summers Kiss' exhibits a low-growing upright habit.
3. *Gaillardia* 'Summers Kiss' exhibits large daisy-like flowers.
4. *Gaillardia* 'Summers Kiss' flowers open pink-orange color and age to a melon.
5. *Gaillardia* 'Summers Kiss' exhibits medium-green foliage.
6. *Gaillardia* 'Summers Kiss' is 46–62 cm. in height and 31–46 cm. in width at maturity when grown in the ground. After one season's growth in a 2 liter container, 'Summers Kiss' is approximately 39 cm in height and 30 cm in width.
7. *Gaillardia* 'Summers Kiss' is reproduced asexually.
8. *Gaillardia* 'Summers Kiss' is hardy to USDA Zone 5.

BRIEF DESCRIPTION OF THE DRAWINGS

The accompanying drawings illustrate the overall appearance of the new *Gaillardia* plant 'Summers Kiss' showing the colors as true as it is reasonably possible to obtain in colored reproductions of this type. Colors in the drawings may differ from the color values cited in the detailed botanical description, which more accurately describes the actual colors of the new variety 'Summers Kiss'. The drawings were made of plants that were grown in a greenhouse and planted in summer in a cultivated area of Maryland. The plants were 12-months old at the time and planted in the ground from 2-liter containers.

The drawing labeled as FIG. 1 illustrates the entire plant in bloom from a side perspective.

The drawing labeled as FIG. 2 illustrates a close-up view of the flower.

Drawings were made using conventional techniques and although flower and foliage colors may appear different from actual colors due to light reflectance, they are as accurate as possible by conventional photography.

BOTANICAL DESCRIPTION OF THE PLANT

The following is a detailed botanical description of the new *Gaillardia* cultivar 'Summers Kiss'. Observations, measurements, values and comparisons were compiled in Arroyo Grande Calif. from a 6-month-old plant in a 2-liter container that was greenhouse grown. Color determinations are made in accordance with The 2001 Royal Horticultural Society Colour Chart from London England, except where general color terms of ordinary dictionary significance are used. In the Compositae family, under which *Gaillardia* is classified, the commonly referred to "flower" is actually the inflorescence, and made up of smaller ray flowers and disc florets. For ease of clarification the common term "flower" is used here to designate a category of description. Under this category is the detailed botanical description of the parts of the inflorescence, which is commonly referred to as the "flower" of this plant.

Botanical classification:
- *Genus.*—*Gaillardia.*
- *Species.*—*grandiflora.*
- *Cultivar.*—'Summers Kiss'.
- *Common name.*—Blanket flower.

Parentage: *Gaillardia* 'Summers Kiss' is a chance seedling that resulted from the open pollination of the following presumed parent plants:
- *Seed parent.*—*Gaillardia* 'Goblin'.
- *Pollen parent.*—*Gaillardia* 'Goblin'.

Propagation method: Softwood cuttings.
Rooting habit: Fine.
Vigor: Vigorous.
Time to develop roots: 10 days to 2 weeks are needed for an initial cutting to develop roots. Air temperature is not critical.
Crop time: 8 weeks are needed to produce a finished 4-inch container and 6 months are needed to produce a finished 2-liter container from a rooted cutting.
Growth habit: Upright and low-growing habit.
Suggested container size: 4-inch and 2-liter containers.
Use: Ornamental landscape plant or container plant.
Type: Herbaceous perennial.
Height of plant:
- *At maturity, in the ground.*—46 cm–62 cm.
- *After one season's growth in a 2 liter container.*—39 cm.

Width of plant:
- *At maturity, in the ground.*—31 cm–46 cm.
- *After one season's growth in a 2 liter container.*—30 cm.

Cultural requirements: Grow in full sun with moderate water and good drainage. Performs well in heat and poor soils.
Hardiness: USDA Zone 5.
Pest and disease susceptibility: Plant is susceptible to aphids.
Special growing requirements: Performs poorly in waterlogged soils.
Stem:
- *Branching habit.*—Basal branching.
- *Stem color.*—144A.
- *Stem dimensions.*—14 cm in length and 4 mm. in width.
- *Stem shape.*—Cylindrical.
- *Stem surface.*—The surface is pubescent and exhibits longitudinal ridges.
- *Internode length.*—Internode length is 4 cm.

Foliage:
- *Type.*—Evergreen.
- *Leaf arrangement.*—Alternate.
- *Single or compound.*—Single.
- *Leaf division.*—Simple.
- *Leaf blade.*—Plane.
- *Margin.*—Entire.
- *Leaf shape.*—Elongated obovate.
- *Leaf length.*—8 cm. in length.
- *Leaf width.*—2 cm. in width.
- *Leaf base.*—Attenuate.
- *Leaf apex.*—Rounded.
- *Leaf venation pattern.*—Pinnate.
- *Vein color* (*abaxial surface*).—147C.
- *Vein color* (*adaxial surface*).—147D.
- *Leaf surface* (*abaxial surface*).—Pubescent.
- *Leaf surface* (*adaxial surface*).—Pubescent.
- *Color of pubescence.*—156D.
- *Leaf attachment.*—Petiolate.
- *Petiole dimensions.*—8 cm. in length and 4 mm. in diameter.
- *Petiole shape.*—Sulcate.
- *Petiole color.*—A combination of colors starting with 147D near the stem and gradually darkening to 147C, then 147B closer to the leaf.
- *Durability of foliage to stress.*—Moderate.
- *Presence of stipules or spines.*—None.
- *Leaf color* (*adaxial surface*).—147B (all stages).
- *Leaf color* (*abaxial surface*).—147B (all stages).
- *Fragrance.*—None.

Flower:
- *Inflorescence.*—Solitary.
- *Aspect.*—Facing upward.
- *Dimensions of inflorescence.*—7 cm. in diameter and 5 cm. in height.
- *Quantity of flowers per inflorescence.*—Approximately 75 disc florets.
- *Flower shape.*—Radiate capitate.
- *Quantity of flowers and buds per plant.*—Approximately 75 to 100.
- *Natural flowering season.*—From mid summer to fall.
- *Lastingness of an individual bloom.*—Approximately 5–7 days in full sun, or 7–10 days in shade or partial shade.
- *Peduncle dimensions.*—15 cm in length and 4 mm. in width.
- *Peduncle shape.*—Cylindrical.
- *Peduncle surface.*—Pubescent and having elongated ridges.
- *Peduncle color.*—144A.

*Peduncle strength.*—Moderate.
*Bud shape.*—Acrescent.
*Bud dimensions.*—At any given time during the bloom period buds range in size from 1 cm. to 2 cm. in diameter and 1 cm. in length.
*Bud color.*—Both 147B and 17D are present.
*Bud surface.*—Lanate.
*Flower (radiate heads) dimensions.*—5 cm. in diameter and 1 cm. in length.
*Self-cleaning or persistent.*—Self-cleaning.
*Petal (ray flower) texture (both adaxial and abaxial surfaces).*—Slightly plicate.
*Petal (ray flower) surface (abaxial surface).*—Pubescent.
*Petal (ray flower) surface (adaxial surface).*—Glabrous.
*Petal (ray flower) arrangement.*—Radiate.
*Number of petals (ray flowers).*—Thirteen in number.
*Fused or unfused.*—Unfused.
*Ray flower margins.*—Entire.
*Ray flower shape.*—Fan-shaped.
*Ray flower apex.*—The apex is lobed and each lobe exhibits a rounded tip.
*Ray flower base.*—Attenuate.
*Ray flower dimensions.*—2 cm. in length and 1.5 cm. in width at the widest part.
*Ray flower color (when first opening).*—25D.
*Ray flower color on adaxial surface (when fully opened).*—The following colors are all present, 17D at the tips, 25D at the base of the petals and dark orange veining that is N30A.
*Ray flower color on abaxial surface (when fully opened).*—The following colors are all present, 17D at the tips, 25D at the base of the petals and dark orange veining that is N30A.
*Dimensions of phyllaries.*—4 cm. in diameter and 1 cm. in length.
*Color of phyllaries.*—147B.
*Involucral bract arrangement.*—Whorl.
*Number of involucral bracts.*—24 in number.
*Involucral bract shape.*—Ovate.
*Involucral bract margin.*—Entire.
*Involucral bract apex.*—Apiculate.
*Involucral bract base.*—Truncate.
*Involucral bract dimensions.*—1.50 cm. in length and 1 cm. in width.
*Involucral bract color (adaxial surface).*—147B.
*Involucral bract color (abaxial surface).*—147B.
*Involucral bract surface (abaxial surface).*—Lanate.
*Involucral bract surface (adaxial surface).*—Pubescent.
*Flower fragrance.*—Slightly sweet scent.
*Disc florets (immature in center).*—Many.
*Disc floret size (mature and immature).*—Small and inconspicuous.
*Surface of disc florets (immature and mature).*—Lanate.
*Disk floret color (immature in center).*—17A.
*Disk floret color (mature at periphery of center).*—34B.

Reproductive organs:
*Stamens.*—Approximately five to each disc floret with filaments adnate to the corolla of each disc floret.
*Anther dimensions.*—0.75 mm. in width and 0.75 mm. in length.
*Anther color.*—16A.
*Anther shape.*—Connate.
*Quantity of pollen.*—Large amount.
*Pollen color.*—16A.
*Chaff.*—One per each disc floret.
*Chaff color.*—156D.
*Chaff dimensions.*—Less than 0.50 mm. in length and less than 0.25 mm. in width.
*Pistil color.*—10B.
*Pistil dimensions.*—15 mm. in length and 0.50 mm. in width.
*Stigma shape.*—Bifid.
*Style color.*—155D.
*Style dimensions.*—5 mm. in length and 0.50 mm in width.
*Style shape.*—Filament.
*Ovary.*—Inferior.

Seed:
*Quantity.*—50–75 seeds per flower.
*Color.*—165B.
*Dimensions.*—0.25 mm. in width and 0.25 mm. in length.
*Shape.*—Obpyramidal cypsela.
*Form.*—Pappus of 8–12 awned scales.

I claim:

1. A new and distinct cultivar of *Gaillardia* plant named 'Summers Kiss' as described and illustrated.

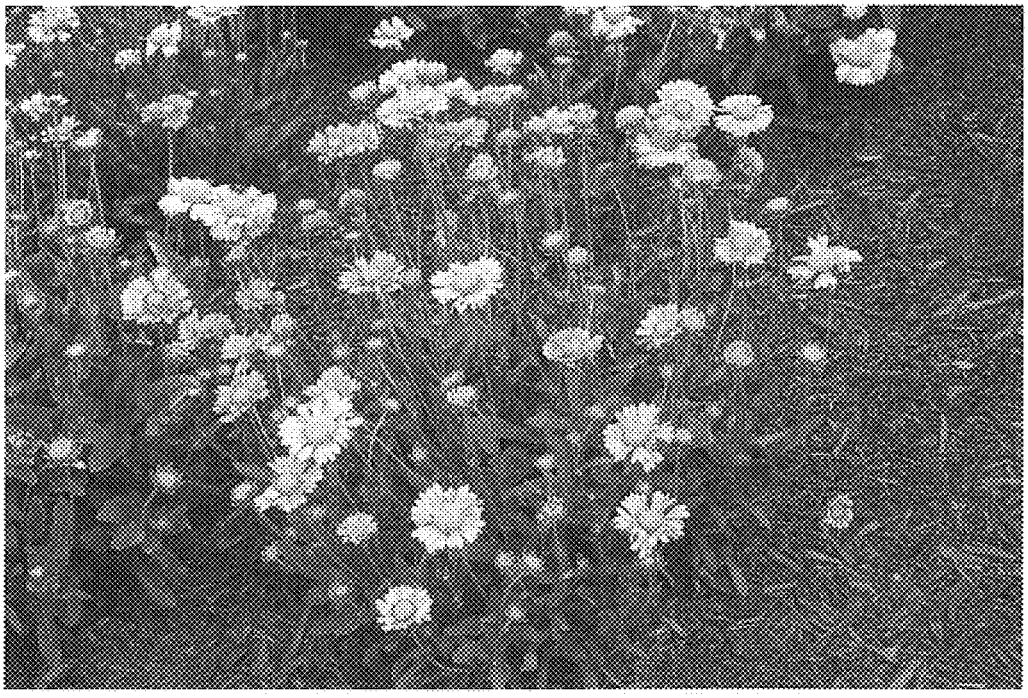

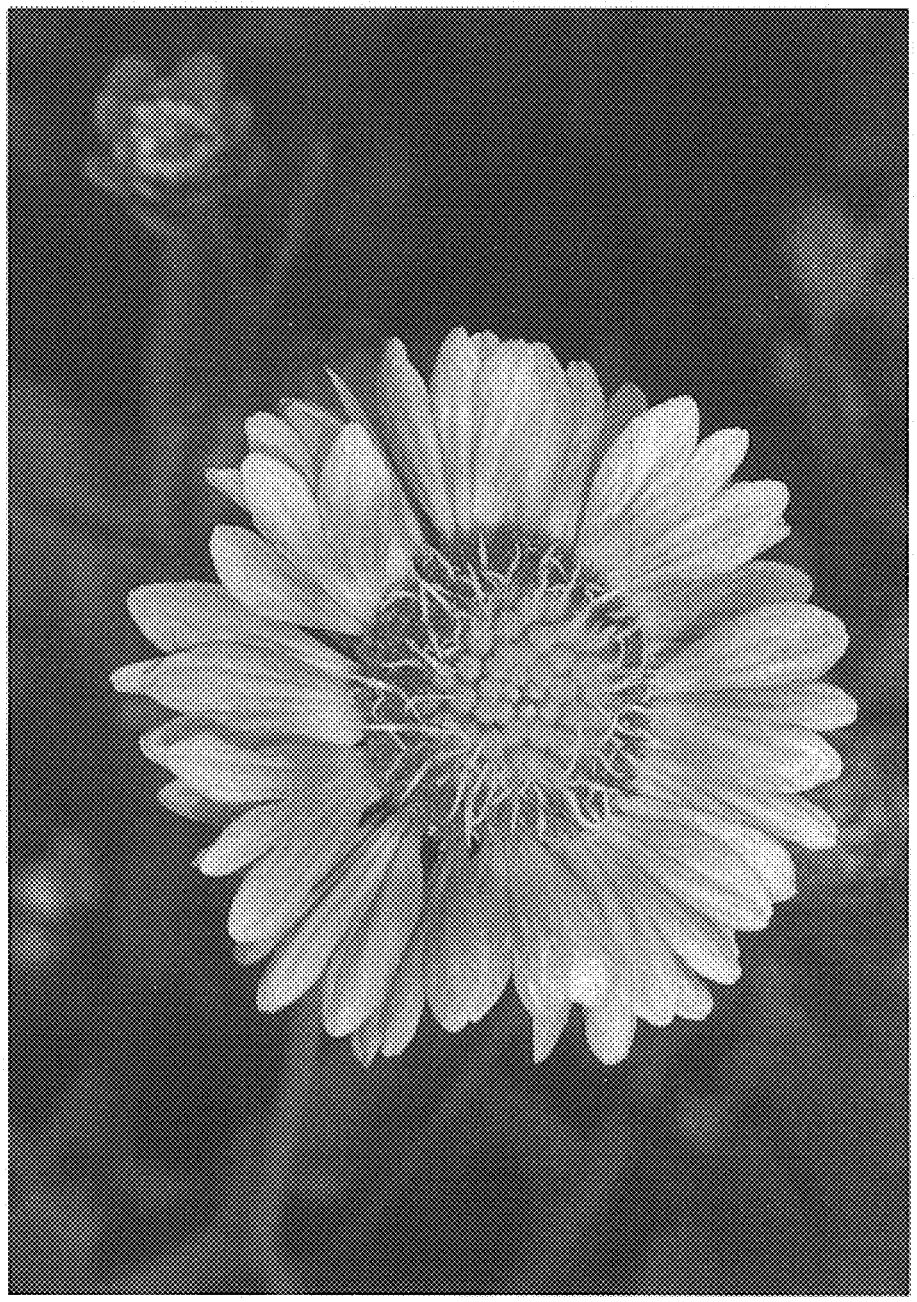

* * * * *